(12) United States Patent
Miles et al.

(10) Patent No.: US 8,241,309 B2
(45) Date of Patent: Aug. 14, 2012

(54) CANNULATION APPARATUS AND METHOD

(75) Inventors: Scott D. Miles, Sandy, UT (US); Kent F. Beck, Layton, UT (US); Timothy R. Nieman, North Salt Lake, UT (US)

(73) Assignee: World Heart Corporation, Salt Lake City, UT (US)

( * ) Notice: Subject to any disclaimer, the term of this patent is extended or adjusted under 35 U.S.C. 154(b) by 3303 days.

(21) Appl. No.: 10/186,307

(22) Filed: Jun. 28, 2002

(65) Prior Publication Data

US 2003/0023255 A1  Jan. 30, 2003

Related U.S. Application Data

(60) Provisional application No. 60/301,795, filed on Jun. 29, 2001.

(51) Int. Cl.
*A61B 17/08* (2006.01)
(52) U.S. Cl. ........................................................ 606/153
(58) Field of Classification Search .......... 606/153–156; 604/34, 4.01, 6.1
See application file for complete search history.

(56) References Cited

U.S. PATENT DOCUMENTS

| | | | | |
|---|---|---|---|---|
| 3,552,712 A * | 1/1971 | Whitlock | ........................... | 251/5 |
| 3,860,300 A | 1/1975 | Lyman | ........................... | 308/10 |
| 4,312,493 A * | 1/1982 | Stauffer | ........................... | 251/8 |
| 4,524,802 A * | 6/1985 | Lawrence et al. | ............. | 137/595 |
| 4,610,664 A * | 9/1986 | Harle | ........................... | 604/119 |
| 4,683,391 A | 7/1987 | Higuchi | ........................ | 310/90.5 |
| 4,688,998 A | 8/1987 | Olsen et al. | .................... | 417/356 |
| 4,697,785 A * | 10/1987 | Tuseth | ........................... | 251/9 |
| 4,718,634 A * | 1/1988 | Bond | ........................... | 251/117 |
| 4,769,031 A | 9/1988 | McGough et al. | ................. | 623/1 |
| 4,794,928 A | 1/1989 | Kletschka | | |
| 4,795,446 A * | 1/1989 | Fecht | ........................... | 604/264 |
| 4,863,461 A | 9/1989 | Jarvik | ........................... | 623/3 |
| 5,041,131 A | 8/1991 | Nagase | | |
| 5,044,897 A | 9/1991 | Dorman | .................... | 417/423.7 |
| 5,055,005 A | 10/1991 | Kletschka | .................... | 417/356 |
| 5,112,202 A | 5/1992 | Oshima et al. | ................ | 417/423 |
| 5,186,431 A * | 2/1993 | Tamari | ........................... | 251/5 |
| 5,195,877 A | 3/1993 | Kletschka | .................... | 417/356 |
| 5,290,306 A | 3/1994 | Trotta et al. | | |
| 5,302,874 A | 4/1994 | Pinkerton | .................... | 310/90.5 |
| 5,326,344 A | 7/1994 | Bramm et al. | ................... | 623/3 |
| 5,336,051 A * | 8/1994 | Tamari | ........................... | 417/19 |
| 5,385,581 A | 1/1995 | Bramm et al. | ................... | 623/3 |
| 5,470,208 A | 11/1995 | Kletschika | .................... | 417/356 |
| 5,488,958 A | 2/1996 | Topel et al. | | |

(Continued)

FOREIGN PATENT DOCUMENTS

WO    WO 99/53974    10/1999

*Primary Examiner* — Darwin Erezo
(74) *Attorney, Agent, or Firm* — Holland & Hart LLP (57) ABSTRACT

A remote cannulation assembly is disclosed for rapidly cannulating a body part such as a heart during a medical procedure. Cannulation is often conducted in procedures such as the installation of a ventricular assist device. The cannulation assembly of the invention utilizes an isolation valve to create a sealed fluid environment for the procedure. The invention further includes a coring assembly that may be used with the cannulation apparatus. Methods of cannulating a heart or other body part are also disclosed in which the risk of emboli is reduced. Additionally, methods of connecting and disconnecting two fluid conducting elements are disclosed.

21 Claims, 7 Drawing Sheets

U.S. PATENT DOCUMENTS

| | | | |
|---|---|---|---|
| 5,576,587 A | 11/1996 | Takahashi et al. | 310/90.5 |
| 5,666,014 A | 9/1997 | Chen | 310/90.5 |
| 5,685,700 A | 11/1997 | Izraelev | 417/423.7 |
| 5,722,429 A | 3/1998 | Larson, Jr. et al. | 128/899 |
| 5,762,624 A * | 6/1998 | Peters | 604/6.06 |
| 5,777,414 A | 7/1998 | Conrad | 310/90.5 |
| 5,783,885 A | 7/1998 | Post | 310/90.5 |
| 5,814,005 A | 9/1998 | Barra et al. | |
| 5,840,070 A | 11/1998 | Wampler | 604/131 |
| 5,911,558 A | 6/1999 | Nakazeki et al. | 415/118 |
| 5,928,131 A | 7/1999 | Prem | 600/16 |
| 5,938,412 A | 8/1999 | Izraelev | 417/423.7 |
| 5,968,053 A | 10/1999 | Revelas | 606/108 |
| 6,001,056 A | 12/1999 | Jassawalla et al. | 600/16 |
| 6,015,275 A | 1/2000 | Suzuki et al. | 417/423.12 |
| 6,033,427 A | 3/2000 | Lee | |
| 6,039,078 A * | 3/2000 | Tamari | 138/30 |
| 6,074,180 A | 6/2000 | Khanwilkar et al. | 417/356 |
| 6,080,133 A | 6/2000 | Wampler | 60/131 |
| 6,083,237 A | 7/2000 | Huitema et al. | |
| 6,129,660 A | 10/2000 | Nakazeki et al. | 600/17 |
| 6,146,325 A * | 11/2000 | Lewis et al. | 600/16 |
| 6,244,835 B1 | 6/2001 | Antaki et al. | 417/356 |
| 6,266,550 B1 | 7/2001 | Selmon et al. | |
| 6,290,639 B1 | 9/2001 | Mussivand et al. | |
| 6,293,901 B1 | 9/2001 | Prem | 600/17 |
| 6,375,607 B1 | 4/2002 | Prem | 600/17 |
| 6,394,769 B1 | 5/2002 | Bearnson et al. | 417/423.7 |
| 6,416,527 B1 | 7/2002 | Berg et al. | |
| 6,475,222 B1 | 11/2002 | Berg et al. | |
| 6,712,831 B1 | 3/2004 | Kaplan et al. | |
| 2002/0045846 A1 | 4/2002 | Kaplon et al. | 604/9 |

* cited by examiner

CANNULATION APPARATUS AND METHOD

RELATED APPLICATIONS

This application claims the benefit of U.S. Provisional Application Ser. No. 60/301,795, filed Jun. 29, 2001, entitled "Remote Cannulation Apparatus and Method." This application is incorporated herein by reference.

BACKGROUND OF THE INVENTION

1. Field of the Invention

The present invention relates to procedures and apparatus to assist in installing and positioning a blood pump such as a left ventricular assist device, right ventricular assist device, total artificial heart, or other devices. More specifically, the present invention relates to methods and apparatus for rapidly cannulating a heart to allow connection to such devices.

2. Description of Related Art

Historically, many treatments for severe forms of heart disease involved some form of open-heart surgery. Open-heart surgeries are historically costly, and generally require extended periods of convalescence. In addition, open-heart surgeries often required either large transfusions of blood to a patient, or the banking of the patient's blood for months in advance due to the high amount of blood loss often involved in the surgery.

In more recent years, in heart surgery, as in many other surgical procedures, efforts have been made to discover faster, less invasive methods which require smaller incisions into a patient's chest cavity and less loss of blood. Such procedures often reduce the recovery time associated with a surgery, and may also improve the survival rate associated with the surgery. In these procedures, the use of specialized tools and procedures drew a new wave of attention to taking special care to prevent complications.

One specific area of concern was complications stemming from the introduction of particles such as air bubbles, clotted blood, or small pieces of tissue, into the bloodstream of the patient. Such debris may travel through the circulatory system and lodge in narrower vessels of tissues such as the brain, cutting off blood circulation. These "emboli" may cause severe complications in a patient, in some cases including death.

Current procedures for heart surgeries including the implantation of left ventricular assist devices (LVAD), right ventricular assist devices (RVAD), total artificial hearts (TAH), as well as other devices, require major incursions into the patient's body and circulatory system. Generally, the patient's heart has been accessed through the sternum. Such surgery exposes the patient to a substantial risk of complications such as introduction of air into the circulatory system, bleeding, and air emboli. Such complications may result in serious patient injury, or even death. Thus, there is a need in the art for methods and apparatus for cannulating the heart and attaching a heart assist/replacement device that minimize the risk of introducing air into the patient's circulatory system, and also reduce the high loss of blood incident to such procedures.

Accordingly, it would be an advantage in the art to provide an apparatus for rapidly coring a body part such as the heart with minimal blood loss. It would be a further improvement to provide methods of using such an apparatus to core such a body part. It would also be an improvement in the art to provide a device for remotely cannulating a body part, including an apparatus for remotely cannulating a heart to permit installation of a heart assist or replacement device. It would be still another improvement in the art to provide methods for using such a device. It would also be an improvement in the art to provide various isolation valves to allow coring and/or cannulation of a body part while preventing the introduction of air emboli into the circulatory system of the patient, while preventing excessive loss of blood. It would also be an improvement in the art to provide methods and apparatus for connecting or disconnecting a device to a cannula already in the system without allowing excessive blood loss or the introduction of air.

Such methods and apparatus are disclosed herein.

SUMMARY OF THE INVENTION

The apparatus and methods of the present invention have been developed in response to the present state of the art, and in particular, in response to the problems and needs in the art that have not yet been fully solved by currently available methods and apparatus for coring and cannulating a body part such as a heart, as well as methods and apparatus for installing a heart assist or replacement device. Thus, the present invention provides apparatus and methods for rapidly coring and cannulating a body part such as the heart with minimal risk of air emboli, thus also allowing for the installation of a heart assist or replacement device.

Some current treatments for heart disorders or diseases call for the installation of ventricular assist devices or heart replacement devices. Previous methods for installing such devices required invasive procedures to create a large opening in the chest cavity of the patient to allow installation. Current methods of installation of such devices call for cardiovascular bypass methods to be used in order to reduce the risk of air emboli during the coring of the heart and the insertion of the device.

The method and apparatus of the invention allow the remote installation of ventricular assist devices. Specifically, the method of the invention provides a rapid and/or remote or minimally invasive method for coring the left ventricular apex of the heart, removing the core, and attaching a ventricular inflow cannula to the heart. When used in surgeries in which a normal incision has been made, as well as when used remotely, the method decreases the risk of air emboli and eliminates the need for cardiovascular bypass. The method may additionally reduce the loss of blood involved in such surgeries, and may improve the comfort of the patient by minimizing the need for thoracotomy (incision into the thorax) or sternotomy (incision into the sternum) by allowing the installation of a device without direct surgical access. This may also reduce the recovery time needed after such a surgical procedure.

In accordance with the invention as broadly described herein, a closed cannulation assembly is first provided. As briefly described above, this assembly allows for the installation of the cannula into a body part such as the heart. This cannulation assembly may include a cannula, a conduit attached to the cannula, and an isolation valve attached to the conduit. In some embodiments of the invention, the cannulation assembly may further include a sealed chamber for holding other parts of the assembly, and possibly for receiving the core taken from the body part. These components may be attached to each other using a sealed chamber to prevent blood loss. The sealed chamber may also accept the core removed from the body part. It may also serve as a guide for the tools during the cannulation procedure.

The cannula is provided to pass through a hole made in a body part, such as the heart, to allow a fluid to be diverted from the body part. In a preferred application, the method is applied to the heart, which is cannulated, allowing the diversion of blood flow from the heart through the cannula.

The cannula of the cannulation assembly may be generally cylindrical in shape and configured to securely attach to a mounting assembly previously mounted to the body part. In some embodiments this may include a retaining groove which integrates with a lock on the mounting assembly. The cannula may be rigid or flexible in its construction. The cannula may also include external threads to allow it to securely integrate with the mounting assembly.

The conduit of the cannulation assembly has a first end which is configured to be coupled to the cannula such that the cannula and the conduit are placed in fluid communication. The conduit of the cannulation assembly may be flexible to allow customized placement when attached to a heart assist or replacement device, or it may be rigid to guide the proper placement of such devices in the body of a patient.

In its various embodiments, the isolation valve of the cannulation assembly may be positioned about any joint of the cannulation assembly at which a fluid or gas may exit or enter the system. In some embodiments, the isolation valve may span more than one such joint. Examples of such attachment include attachment of the isolation valve to the apical ring attached to the heart, or to an end of the conduit. In another example, the isolation valve may be connected at the joint between the cannula and the conduit. Alternately, the isolation valve may be positioned at joints of sections of conduit, or between a joint in the conduit and an implantable blood pump. The isolation valve is configured to be actuatable between an open position that permits passage of fluid through the valve into the conduit, and a closed position that prevents fluid flow through the conduit.

In one configuration, the isolation valve includes a tubular housing and a blocking member for occluding the valve. The blocking member may be a rotatable plug with a bore through it. To open the isolation valve, the blocking member may be rotated such that the bore is aligned with the tubular housing. To close the isolation valve, the blocking member may be rotated such that the bore is out of alignment with the tubular housing, thus preventing fluid flow. In this configuration, the isolation valve may be constructed to remain in the patient after installation of the cannula.

Here, the isolation valve may be connected in-line with a cannula or conduit on one side, and with either another component such as a conduit, or the heart assist- or replacement-device on the other side of the isolation valve. Thus, following use of the isolation valve during installation of the cannula and heart assist- or replacement-device, and following the completion of the external circuit from the heart assist device to the aorta, the valve is set in its open configuration. The valve remains in this configuration after this point, thus allowing free flow of blood through the assembly and transmission throughout the body.

In another configuration, the isolation valve includes a tubular housing and a blocking member in the form of a slidable gate. This slidable gate is configured to pass through an orifice placed in the tubular housing, thus bisecting it. To open the isolation valve, the slidable gate may be retracted through the orifice in the tubular housing into a gate housing, thus opening a pathway through the tubular housing. To close the isolation valve, the slidable gate is inserted into the orifice and passed into the tubular housing, occluding it.

In this configuration, the slidable gate is enclosed in a gate housing that surrounds the tubular housing of the isolation valve. The slidable gate and the housing enclosing it may be constructed to be removed after cannulation. To do this, the slidable gate is retracted into the gate housing, the connection between the cannula and conduit or conduit and heart assist or replacement device is made, and the gate housing is separated into two pieces and removed from around the isolation valve. In such isolation valves, the housing of the isolation valve is configured to then be compacted or sealed to close off the orifice provided for the slidable gate.

In still another configuration, the isolation valve of the invention is a flexible sealable cuff that can be placed about portions of the system while they are being joined to each other. Such a cuff may be sealably attached about any joint along the fluid path from the heart to the aorta, including joints at the apical ring, an end of a conduit, cannula, or pump. The cuff may then be sealed in such a fashion that gases and liquids cannot penetrate it. The cuff is flexible in its construction such that it may be clamped shut using tools such as forceps during a surgical procedure to prevent passage of a fluid from one end of the cuff to another. This feature may be useful prior to establishing an air-free environment inside of the cuff. The cuff may be a single unitary component, or it may be composed of multiple segments capable of being sealably united to increase convenience of use. The cuff is useful for making and breaking connections throughout the system, and is usable with previously-installed components that need to be removed without allowing a loss of large amounts of blood or permitting the bloodstream to be exposed to air.

As with the other isolation valves of the invention, the cuff may include at least one de-airing port to allow the interior of the cuff to be de-aired. Preferably, the cuff contains at least two de-airing ports. These de-airing ports allow saline or another suitable fluid to be pumped into the cuff and for all air to be removed from the cuff. Alternatively, the cuff could be de-aired by penetrating it with a needle and removing the air. In some configurations, the cuff could be constructed to re-seal itself upon removal of the needle. Multiple de-airing ports allow the cuff to be divided into sealed compartments using forceps or other instruments capable of providing a compressive force. These individual compartments may be opened and closed, as when inserting or removing objects such as tools, and then de-aired prior to returning them to their original state of being in fluid communication with the remainder of the system.

Additionally, the cuff may be used in the place of the sealed chamber for receiving tools to be removed from the body of the patient and for receiving the core from the heart. Specifically, the object to be removed may be withdrawn into an end of the cuff, and the cuff may be clamped shut behind the object, sealing the system, and allowing removal of the object. After removal of the object, the sealed-off portion of the cuff may be de-aired again and opened up to the system for additional use.

In accordance with the invention as described herein, a coring assembly is next provided. The coring assembly is configured to pass through the remote cannulation assembly of the invention, excise a core from a body part such as the heart, and allow for removal of the core from the body. The coring assembly of the invention comprises a coring assembly housing, a coring tool, and a core retainer.

The coring assembly housing of the invention has two ends, each of which is configured to sealably attach to other surgical tools such as the cannula, isolation valve, or other components of the remote cannulation apparatus of the invention.

The coring tool of the assembly may be a cylindrical cutting tool, a flexible cylindrical cutting tool, a cutter jet, a rotatable blade, or another known cutting means. The coring tool is configured to fit within the coring assembly housing, and to travel through the isolation valve, conduit, and cannula of the remote cannulation assembly. It may thus be configured to be attached to the cannula and/or conduit of the remote cannulation assembly.

In one configuration, the core retainer of the remote coring assembly is helical in shape. The core retainer is configured to travel within the coring tool, and thus through the remote cannulation assembly. The core retainer of the invention is designed to penetrate into the core to be removed from the body part. It holds the core steady while it is excised, and ensures the smooth removal of the core from the body to thus prevent it or portions of it to become emboli, i.e., to enter the bloodstream. The shape of the core retainer causes it to penetrate a core of a wall of the body part to be cored.

The helical head of the core retainer may also include a port connected to a pressure monitoring or fluid sampling port positioned near an outside end of the core retainer. This allows sampling of fluid from, or introduction of fluid into, the body part. This also allows monitoring of pressure at the tip of the core retainer. Fluid sampling or monitoring allows the user to know when the core retainer has completely pierced a wall of the body part to be cored. The core retainer may alternatively comprise an endoscope port to allow monitoring of pressure or to provide influx of fluids into the body part to establish and ensure a positive internal pressure, thereby preventing air emboli.

In other configurations, the core retainer may comprise barbed tips, graspers, expanding structures, or other similar means by which the retention of the core can be established. All such core retainers are characterized by their ability to retain the tissue excised by coring, thereby allowing removal of the excised tissue. Further, in embodiments of the core retainer allowing fluid sampling from the interior of the body part, core retainers will be characterized by their ability to penetrate the body part being cored, thereby accessing an internal face of the outer wall of the body part and any fluid reservoir housed within the body part. Other core retainers do not necessarily travel completely through the outer wall of the body part, instead traveling only partially through to retain the core.

The remote coring assembly of the invention may further comprise a conduit protection sheath. The conduit protection sheath is positioned within the remote coring assembly housing and positioned about the coring tool and the core retainer. This sheath is configured to move slidably within the conduit or cannula of the remote cannulation assembly. The sheath acts to protect the conduit and cannula from the cutting tool and the core retainer.

The invention also includes a method of using a remote cannulation apparatus and a remote coring apparatus to remotely cannulate a body part. The steps of this method may be varied while producing the same result. A first step of the method is to position the cannula of the remote cannulation assembly adjacent to the body part to be cannulated. In this step, the cannula is pressed against the body part so as to create a seal to prevent leakage of air, blood, or saline solution into or out of the bloodstream. In a next step, the cannulation assembly is flooded with saline or other physiological fluid to remove any air. The coring tool is then attached to the isolation valve and similarly flooded to remove any air. The coring tool is then inserted through the isolation valve in its open configuration and guided through the conduit and cannula to abut the body part.

At this point the core retainer is advanced into the body part to be cored to hold the tissue to be removed. Then an opening is formed in the body part by cutting a core in the body part with the coring tool while retaining the core with the core retainer. The core may be removed from the body part at this point. The cannula may then be advanced into the hole, replacing the core. The cannula is moved into its desired position. The coring tool and core retainer may then be withdrawn. The core is thus cut using a coring tool positioned within an inside diameter of the cannula. In some embodiments of the invention, the core is cut coaxially with the cannula.

In methods of the invention using the flexible cuff embodiment of the isolation valve, the method includes additional steps. First, the cannula of the remote cannulation assembly is placed adjacent to the body part to be cannulated. The cannula is pressed against the body part to create a seal to prevent leakage of air, blood, or saline solution into or out of the bloodstream. The cannulation assembly is next flooded with saline or another physiological fluid to remove any air. The flexible cuff isolation valve is attached about the apical ring of the heart on a first end and about an end of the coring tool on another end. The flexible cuff isolation valve and the coring tool are flooded to remove any air. The coring tool is then inserted through the cuff and guided through the conduit and cannula to abut the body part.

As above, the core retainer may be advanced into the body part to be cored to hold the tissue to be removed. An opening is then formed in the body part by cutting a core in it with the coring tool while retaining the core with the core retainer. The core may be removed from the body part at this point. The cannula may then be advanced into the hole, replacing the core. The cannula is moved into its desired position.

Having placed the cannula, the core and/or cannulation tools may be removed into the portion of the isolation valve furthest from the heart. The flexible cuff is clamped in its center region to separate it into two sealed chambers, one containing the core. The core and/or cannulation tools may then be removed.

Following removal of these components, additional components such as the VAD may be placed within the open end of the isolation valve. Following this, the opened portion of the valve is de-aired by flooding it with an acceptable medium, and the cuff is unclamped, and the component such as the VAD may be safely attached to the patient inside the flexible cuff. When all connections have been made, the cuff may be removed. As briefly noted above, such flexible cuffs may be used to break previously-made connections, such as when removing a VAD that has malfunctioned or become worn or damaged. The flexible cuff isolation valve may find application in many surgical procedures in which conduits such as vessels, ducts, or intestines need to be joined without significant exposure to an outside environment, or when the contents of such conduits are desired to be retained and prevented from escaping.

These and other features and advantages of the invention will become more fully apparent from the following description and appended claims. They may also be learned by the practice of the invention as set forth hereinafter.

BRIEF DESCRIPTION OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the apparatus, system, and method of the present invention, as represented in FIGS. 1 through 6, is not intended to limit the scope of the invention, as claimed, but is merely representative of presently preferred embodiments of the invention.

Figure 1:
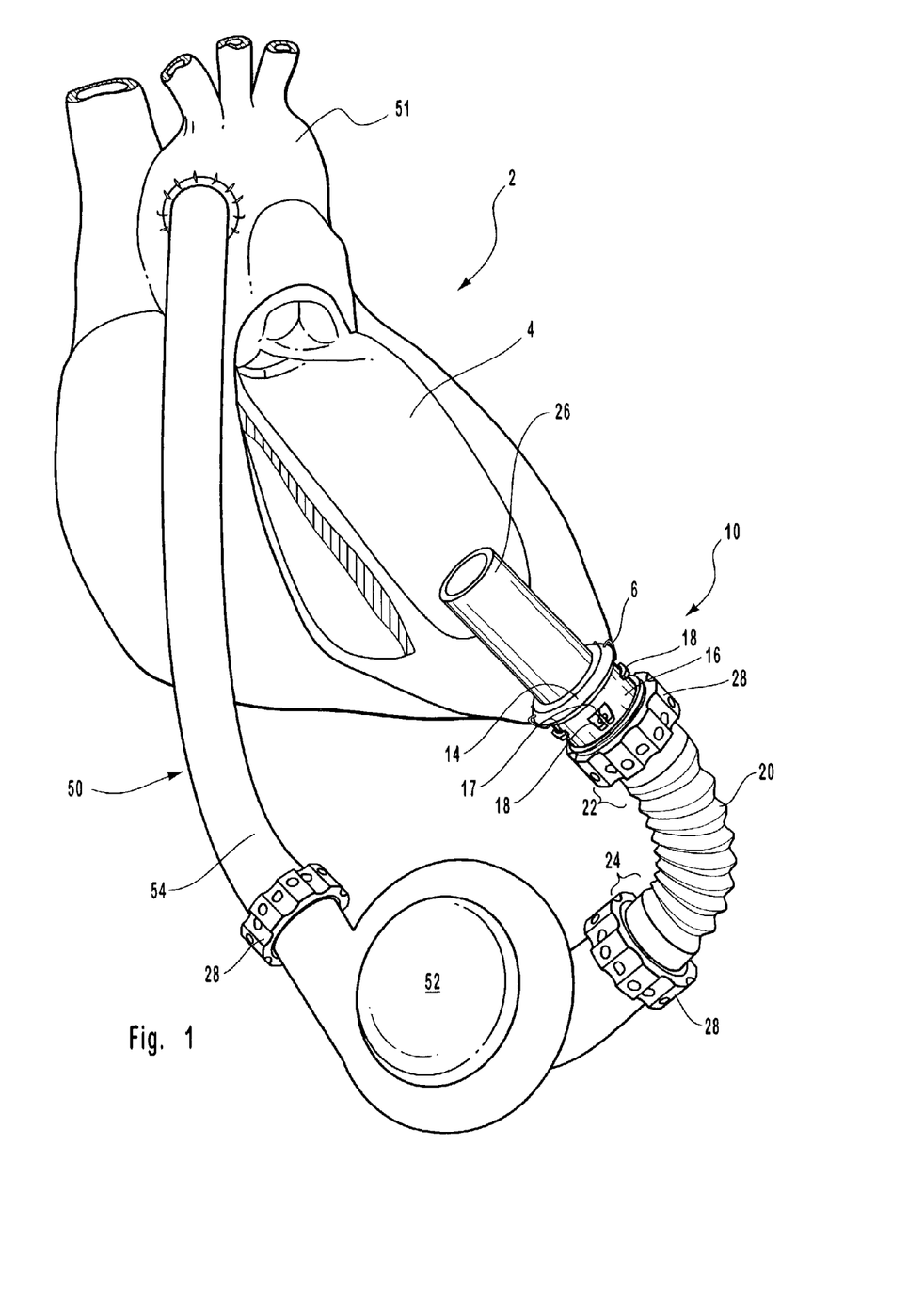
FIG. 1 is a perspective view of a cannulation apparatus of the invention installed in the heart of a human patient in conjunction with a left ventricular assist device.

Referring now to FIG. 1, a remote cannulation assembly 10 of the invention is shown fully installed into a heart 2. The cannulation assembly 10 is shown placed into a left ventricle 4 of a heart 2 and attached to a heart assist or replacement device 52. In turn, the heart assist or replacement device (or "pump") 52 is attached to an output conduit 54 which is attached to an aorta 51. This forms a continuous channel from the left ventricle 4 through the cannulation apparatus 10, pump 52, and output conduit 54 to form an aortic anastomosis 50 that effectively links the ventricle 4 to the aorta. This allows blood to be drawn from the ventricle 4 into the pump 52 and expelled into the output conduit 54, and subsequently into the aorta 51. The pump 52 assists the heart 2 in pumping the blood by providing a forceful flow of blood from the heart 2 into the aorta 51.

The assembly 50 shown in FIG. 1 may be implanted in a patient suffering from an illness such as congestive heart failure. In such a patient, a heart has become unable to provide adequate blood flow to the body. This results in congestion of blood in the patient's body, often resulting in weakness, edema, and shortness of breath. Heart assist or replacement devices such as 52 with the attachment or cannula assemblies 10 are often enlisted to provide added force to the blood flow pumped from the heart.

In the invention, the aortic anastomosis 50 may be created remotely (meaning at a distance from, or not requiring surgeon to touch by hand) using devices available in the art. Specifically, the invention relates to methods and apparatus provided to rapidly insert a cannula 26 into the heart 2 or other body part. These methods are useful when cannulating the heart 2 remotely and when cannulating the heart 2 using traditional surgical access to the heart through the sternum. The invention also relates to methods and apparatus by which this insertion and attachment can be made without risk of emboli such as air bubbles or tissue particles. Such methods are useful in combination with methods and apparatus that allow the remote attachment of the output conduit 54 to the aorta 51. The methods and apparatus of the invention may thus allow placement without need for either a sternotomy or a thoracotomy, and with reduced rates of surgical complications including death.

In order to provide assistance to the heart, a pump device such as the heart assist or replacement device 52 must have access to the interior of the heart 2 and the blood flowing through it. In some applications it is desirable to gain this access in the left ventricle 4 of the heart 2 where the blood has already been oxygenated and is about to be pumped into the aorta 51 to be distributed throughout the patient's body.

The invention thus provides a method and device that allow rapid and sealed access to a chamber in the interior of a heart 2 such as left ventricle 4. Specifically, the invention provides a cannulation device 10 for inserting a cannula 26 into a body part such as the heart 2.

First, an apical ring 12 is provided that may be anchored to the body part using attachments 6. These attachments 6 may include stitches and surgical staples, among others. This attachment is preferably done using remote devices. The apical ring may additionally be sealed using a surgical glue (not shown). The apical ring 12 interacts with a locking ring 18 and the cannula 26 to lock the cannula 26 in position relative to the heart 2 by means of locking ring 18. Locking of the cannula 26 to the heart 2 may be accomplished using a locking ring 18 as shown, or may instead be attached using threads, sutures, or a suitable clamp.

Second, the cannula 26 may include external features such as threads that interact with the apical ring 12. Alternatively, the cannula 26 may include a groove (not shown) that interacts with the locking ring 18. Other external features could be placed on the cannula 26 to allow direct insertion into and/or anchoring with a body part without the use of an apical cuff 12.

The remote cannulation assembly 10 comprises a cannula 26 and a conduit 20 having a first end 22 and a second end 24. The cannula 26 is shown attached to the left ventricle 4 by an apical ring 12 using a locking ring 18. The apical ring 12 includes an attachment ring 14 and a locking stem 16. The attachment ring 14 may be attached to the heart 2 using several methods including stapling and sewing. The locking stem 16 includes slots 17 for engaging the teeth 19 of the locking ring 18 as they are spread by the entry of the cannula 26. The locking ring 18 may be configured to be housed inside or outside of the locking stem within the scope of the invention. The cannula 26 may be connected to the conduit 20 by screw rings 28. Screw rings 28 are configured to link the cannula 26 to the conduit 20 in a sealed manner, while allowing the cannula 26 and the conduit 20 to remain in fluid communication. As a result, blood can be carried from the left ventricle 4 through the cannula 26 and into conduit 20.

Figure 2:
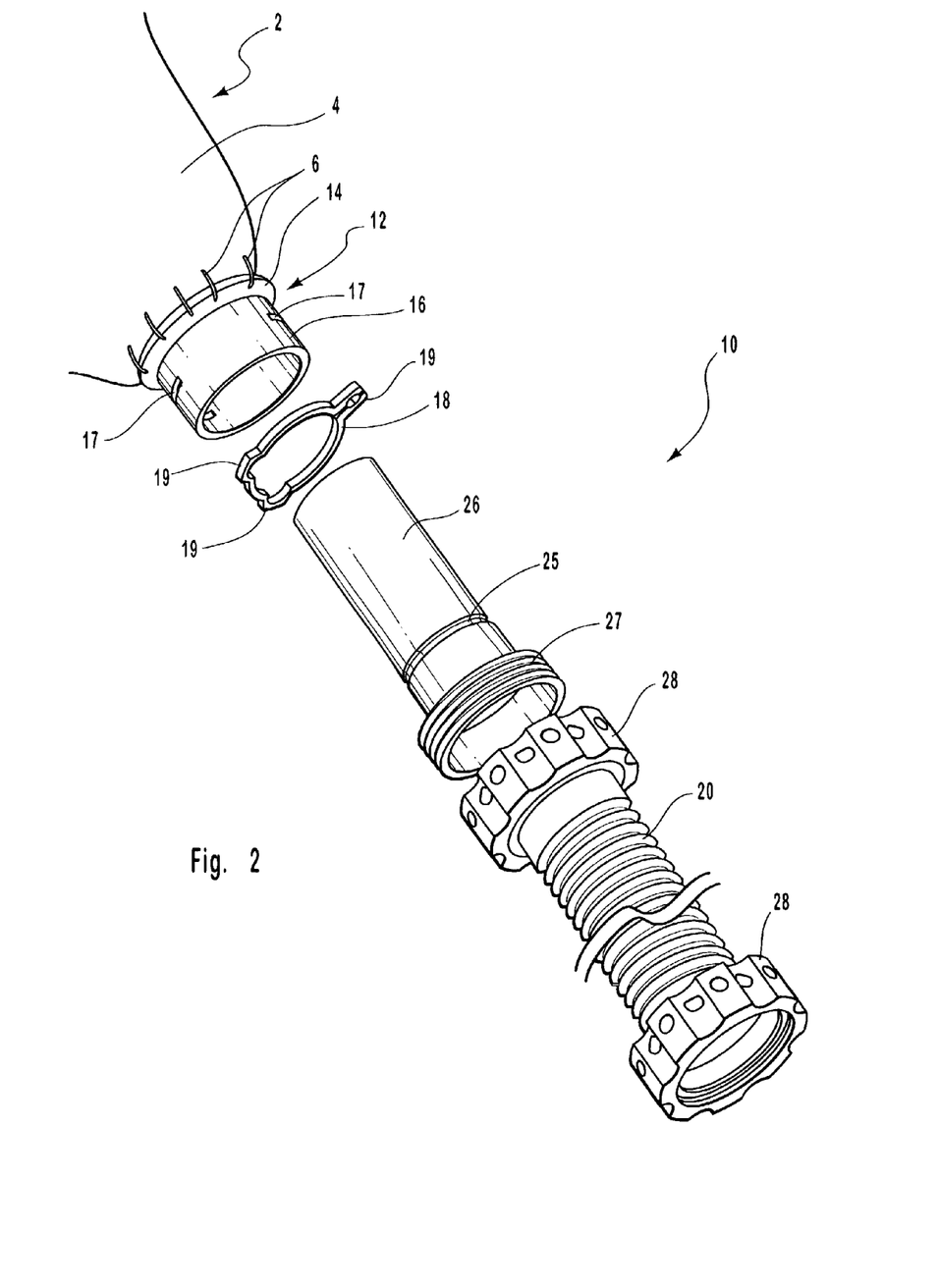
FIG. 2 is an exploded perspective view of the cannulation apparatus of FIG. 1, illustrating the relationship and configuration of the components of the cannulation apparatus.

FIG. 2 is an exploded perspective view of the remote cannulation assembly 10 of the invention. The left ventricle 4 of the heart 2 is shown attached to apical ring 12. Here, the apical ring 12 is shown attached to the heart 2 using stitches 6 placed into the attachment ring 14. The slots 17 of the locking stem 16 are clearly visible. The locking ring 18 is shown having teeth 19. These teeth 19 fit into slots 17 of the locking stem 16 to hold the cannula 26 in place. FIGS. 1 and 2 show the locking ring 18 configured to be positioned inside the locking stem 16. In alternative embodiments, the locking ring 18 is configured to be positioned on the outside of the locking stem 19, and to engage the slots 17 with teeth 19.

The cannula 26 is illustrated as an elongated cylindrical tube. Being thus configured, the cannula 26 may pass through the locking ring 18 and the apical ring 12. In embodiments using either internal or external locking rings, the cannula 26 engages the locking ring 18, affecting its engagement with the slots 17 of the locking stem 16. In some embodiments, the cannula 26 may include a groove 25 to engage the locking ring 18 when the cannula 26 has reached its optimal position. This locks the cannula 26 into place. Alternatively, the cannula 26 may include other surface features such as threads to engage the apical ring 12.

As briefly described relative to FIG. 1, the cannula 26 is attached to the conduit 20 by a screw ring 28 or other suitable method or component that engages threads 27. Similarly, a screw ring 28 connects the conduit 20 to the isolation valve 30. The screw ring 28 is configured to be attached securely to the cannula 26 or the isolation valve 30 in a sealed manner. This allows de-airing of the apparatus without allowing air or blood out of the apparatus into the body of the patient.

The conduit 20 may be flexible or of a set shape and orientation. The conduit 20 conducts blood from the left ventricle 4 of the heart 2 to a pump such as a ventricular assist device ("VAD") 52. The conduit 20 may be linked to the screw rings 28 with seals such that when screw rings 28 are attached to the cannula 26 of the pump 52, or other components, a fluid-tight seal is obtained.

Figure 3:
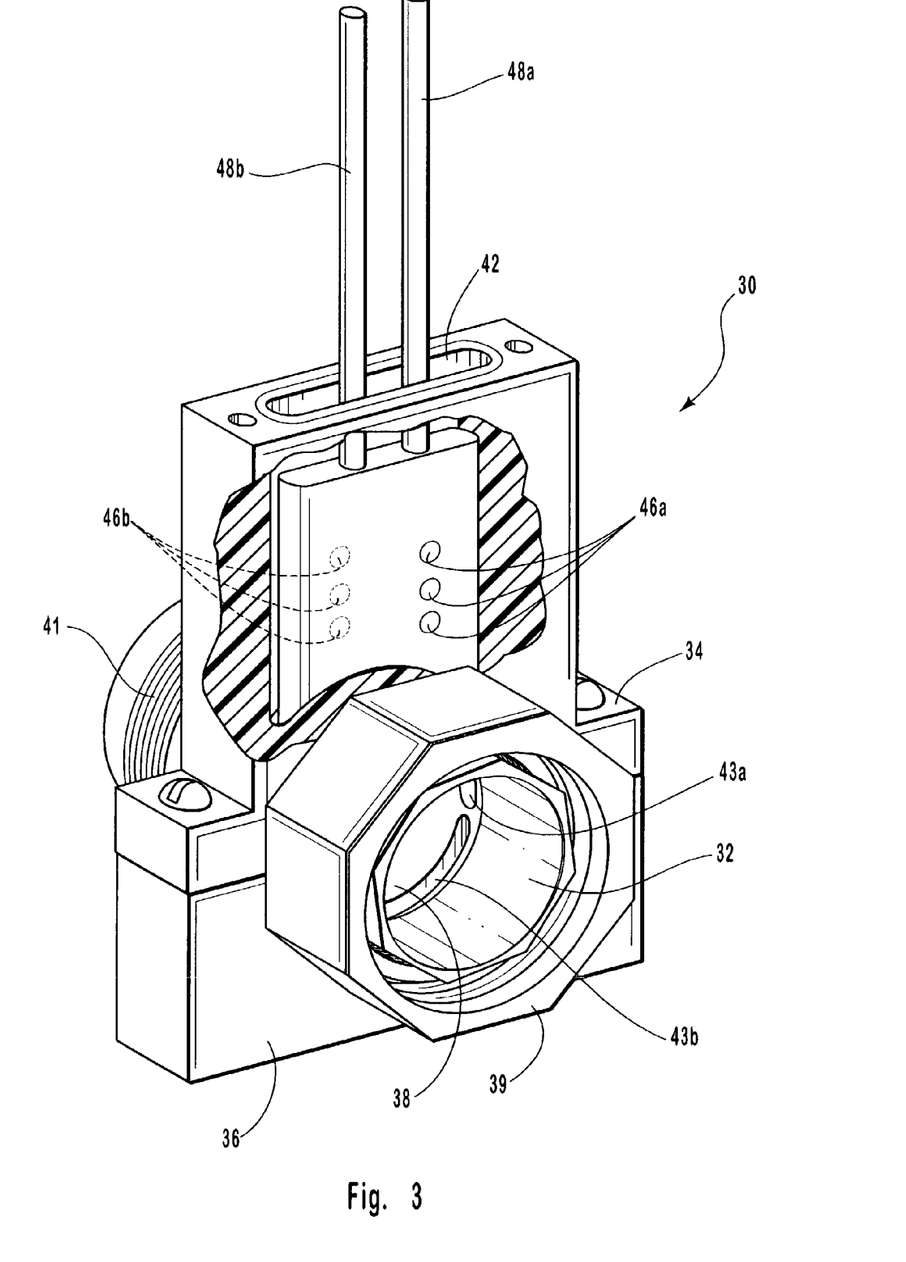
FIG. 3 is a perspective view of an isolation valve of the cannulation apparatus of the invention.

In FIG. 3, an embodiment of the isolation valve 30 of the cannulation assembly 10 of FIG. 1 is shown prior to attachment of the pump 52. The cannulation assembly 10 includes an isolation valve 30 to provide hemostasis (or prevent blood leakage), during use. These isolation valves are also provided with de-airing ports 46a, 46b to allow for removal of air from the remote cannulation system 10 to reduce the risk of air emboli and excessive bleeding. This also reduces the necessity of placing a patient on cardiovascular bypass during such surgeries.

The isolation valve 30 may be attached to the conduit 20 by a screw ring 28, which may engage the threaded joint 41. The isolation valve 30 includes an upper gate housing 34, a lower gate housing 36, and a slidable gate 40. The gate housings 34, 36 attach about a valve channel 38 that is continuous with threaded joint 32 and an attachment link 39. The attachment link 39 is configured to be attached to either a VAD (not shown), a remote cannulation housing, or to other components such as additional conduit. The gate housings 34, 36 contain a gate passage 42 that allows the gate 40 to pass through the housing in a sealed manner. The valve channel 38 also includes at least one gate orifice 43 that allows the gate 40 to pass into and through the valve channel 38 in a sealed manner, thus occluding it. In this way, the isolation valve 30 of the remote cannulation assembly 10 provides the ability to close the system.

The gate 40 includes at least one de-airing port 46a or 46b. As illustrated in FIG. 3, each face of the gate 40 includes several de-airing ports 46a and 46b. These de-airing ports 46 are in fluid communication with catheters 48a and 48b. The catheters 48a and 48b may be used to inject a physiologically acceptable fluid such as blood or saline solution, and to withdraw a fluid, a gas (such as air), and even small particulate matter. Catheters 48a and 48b may be configured to be in fluid communication with opposite sides of the gate 40. This allows for effective de-airing of the system, thus preventing emboli. This configuration also allows tools and components to be attached to and detached from the isolation valve 30 without significant blood loss during the course of a surgery.

Figure 4:
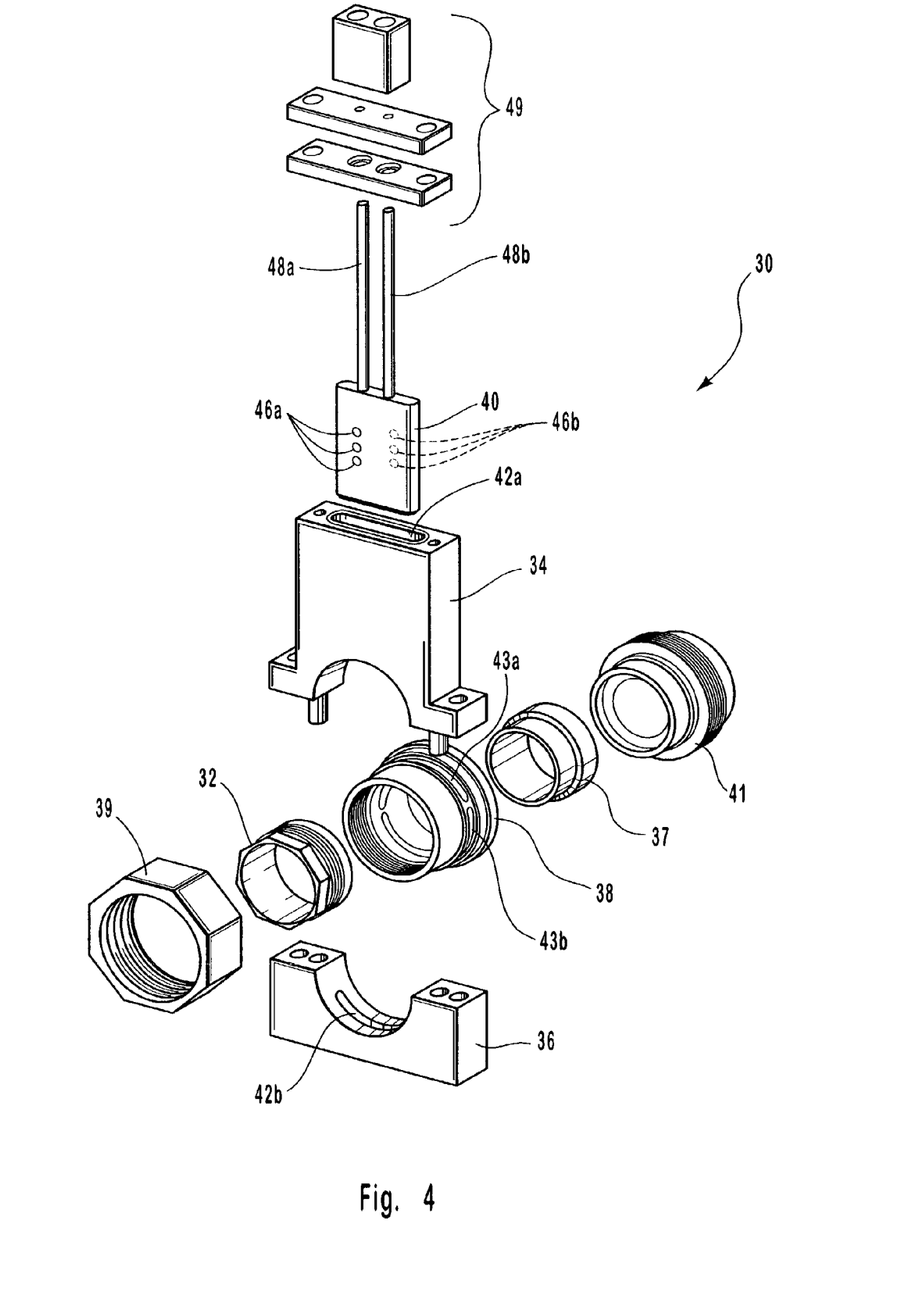
FIG. 4 is an exploded perspective view of a preferred isolation valve of the invention.

FIG. 4 is an exploded perspective view of the isolation valve 30 of the remote cannulation assembly 10. As in FIG. 2, the isolation valve 30 comprises a gate housing having an upper gate housing 34 and a lower gate housing 36 which link together about valve channel 38, enclosing it. When properly installed, the gate passages 42a, 42b of the gate housings 34, 36 align with gate orifices 43a, 43b present on opposite sides of the valve channel 38. The slidable gate 40 may be passed through the gate passage 42a, through the gate orifices 43a, 43b of the valve channel 38, and into the gate passage 42b in a sealed manner. This occludes the valve channel 38 such that fluid may no longer flow through it.

The slidable gate 40 includes at least one de-airing port 46a or 46b. These ports 46a and 46b may simply be orifices in the face of the slidable gate 40 that are in fluid communication with tubes such as catheters 48a and 48b (shown in phantom when within the slidable gate 40) through which air may be removed and a suitable physiological fluid such as saline solution may be introduced. Multiple ports 46a and 46b may be used on a given face of the slidable gate 40 to better facilitate de-airing of the assembly. Preferably, the slidable gate 40 includes de-airing ports 46a and 46b on both faces of the assembly to allow de-airing of the system on both sides of the isolation valve 30. The isolation valve 30 may also have at least one seal plate 49 to provide a seal over the upper and lower gate housings 34, 36.

In some embodiments of the invention, the slidable gate 40 and the gate housing portions 34, 36 are removable after cannulation. In such, the gate housing portions 34 and 36 are separated from each other and detached from around valve channel 38, thus removing the functional valve components of the isolation valve 30. Prior to this, however, the gate orifices 43a, 43b must be closed in order to preserve the integrity of the sealed, de-aired system. This may be accomplished by turning clamp ring 32 to advance it against the gate seal 37 which is sealably connected to conduit 20 (not shown) to seal it against threaded ring 41.

Figure 5:
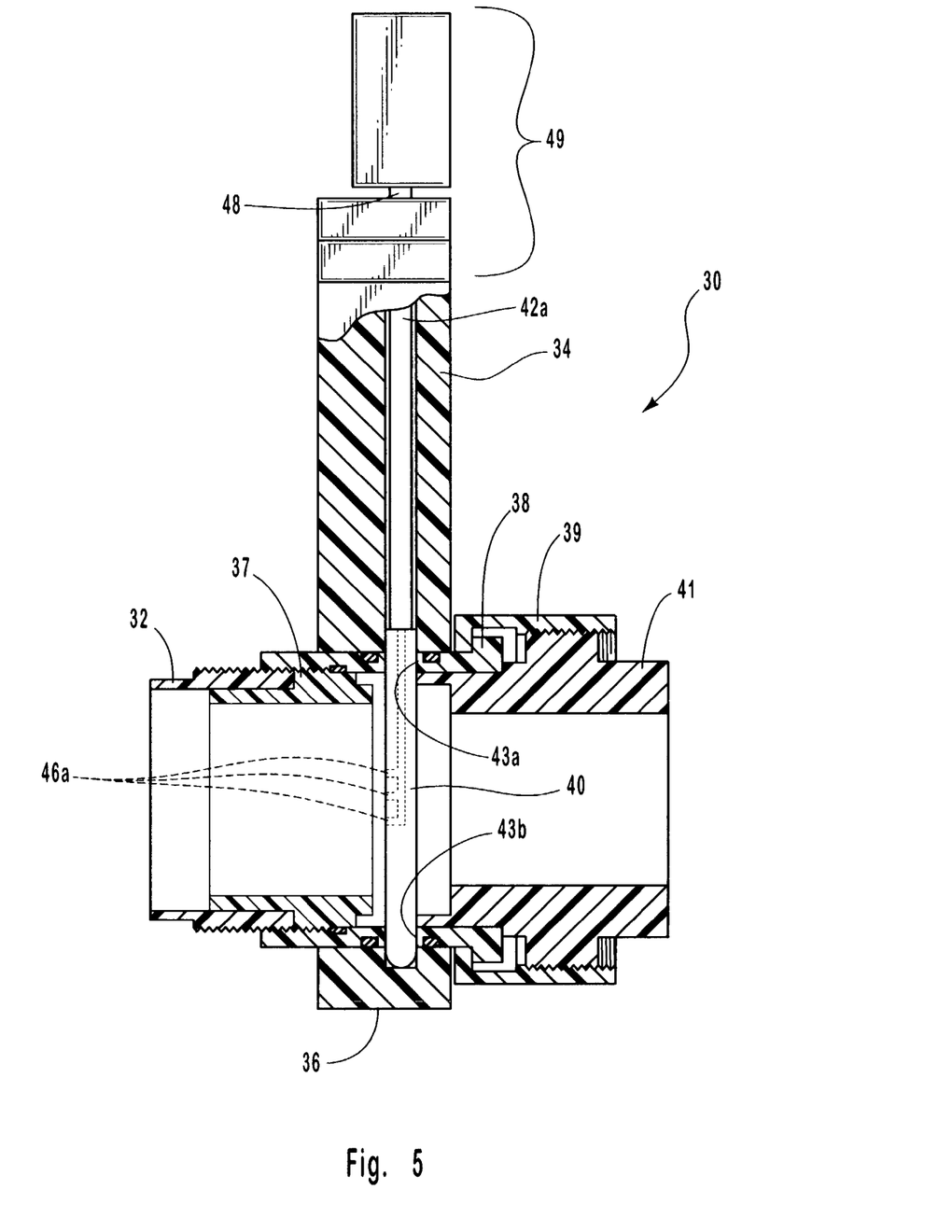
FIG. 5 is a cross-sectional view of the isolation valve of FIG. 4 shown assembled and in its closed position.

FIG. 5 is a cross-sectional view of the isolation valve 30 of FIG. 4, this time assembled and shown with the slidable gate 40 in its closed position. In this view, the interaction of the parts of the isolation valve 30 can be appreciated, and the manner in which the components of the valve 30 maybe shifted to seal the gate orifices 43a, 43b is shown. Specifically, in order to seal the gate orifices 43a, 43b, a gate seal 37 is present in the system which is configured to be actuated by an operator from its valving position, in which the gate passages 43a, 43b are clear, to its sealed position, in which the gate passages 43a, 43b are completely occluded. In the sealed position, blood is prevented from escaping and air is blocked from entering the system.

In FIG. 5, the slidable gate 40 is shown in its closed position, blocking flow of fluid through the valve channel 38. When the slidable gate 40 is open, the gate orifices 43a, 43b may be closed by positioning the gate seal 37 such that it overlaps the gate orifices 43a, 43b, effectively sealing the valve 30 and preventing the closing of the valve 30 using the slidable gate 40. In one embodiment, the gate seal 37 may be positioned by tightening it along the threaded joint or "clamp ring" 32 in concert with valve channel 38. The clamp ring 32 may additionally be coupled to the gate seal 37 to allow the gate seal to be moved to and from its closed position by moving the clamp ring 32. Other methods of positioning a gate seal 37 include clamps, various locking mechanisms, and other means known in the art.

The isolation valve 30 may be sealably attached to the conduit 20 of FIG. 2, the coring assembly (discussed below), or other components such as a ventricular assist device 52. In FIG. 5, several linking mechanisms are shown. First, on one side of the valve channel 38, a simple clamp ring 32 threadably engages internal threads optionally present in the valve channel 38 to adapt the isolation valve 30 to attach to conduit 20 of FIG. 2. In this configuration of the invention, the clamp ring 32 also threadably engages with the gate seal 37. As noted, the clamp ring 32 may be coupled to the gate seal 37 such that progression of the clamp ring 32 allows the gate seal 37 to be opened or closed. The gate seal 37 and the clamp ring 32 are configured to be attached to other elements of the implantable system such as the conduit 20 of FIG. 2 or a ventricular assist device or heart replacement device.

Figure 6:
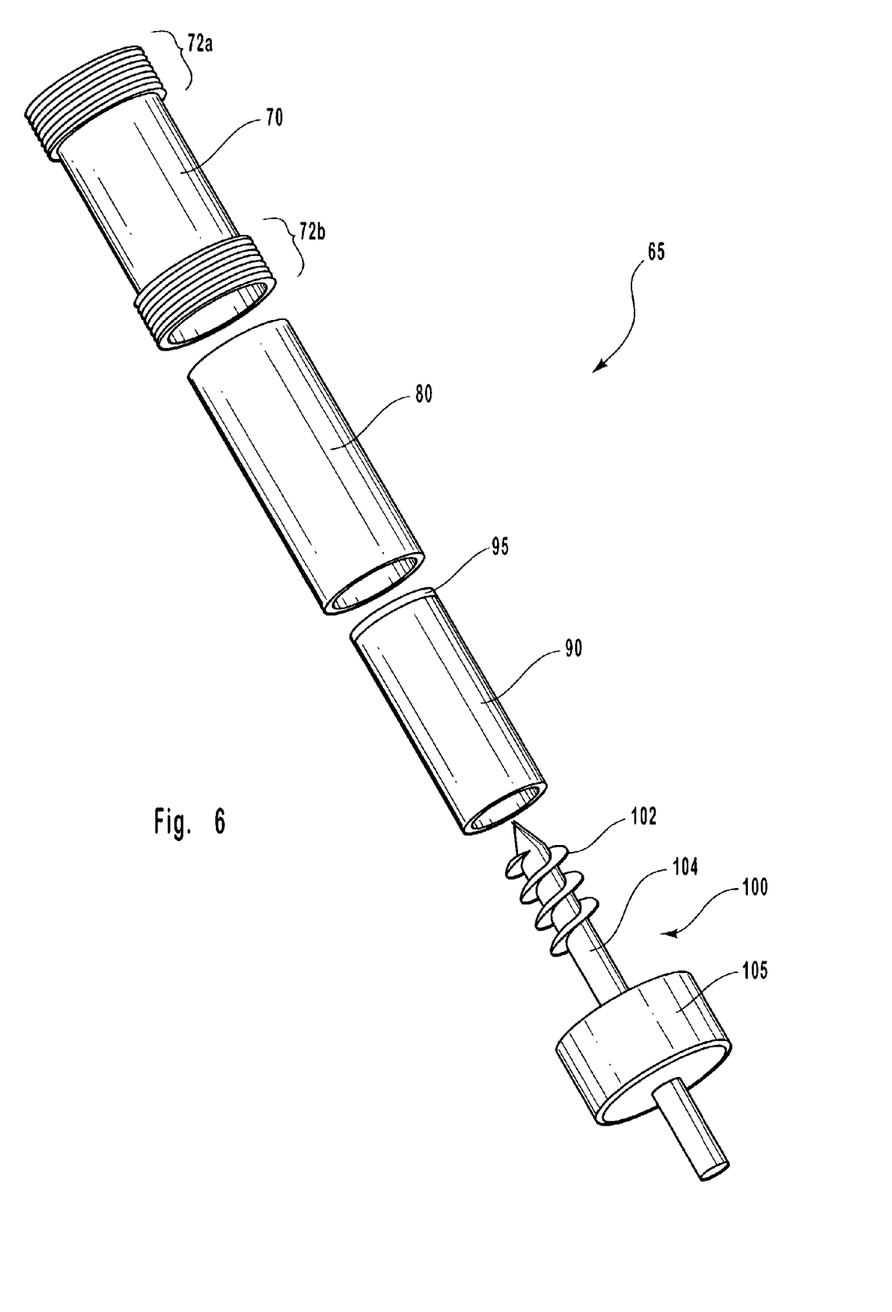
FIG. 6 is an exploded perspective view of the coring device of the invention.

FIG. 6 is an exploded perspective view of the coring assembly 65 of the invention. The coring assembly 65 includes a coring assembly housing 70. The coring assembly housing 70 has attachment regions 72a, 72b configured to be sealably attached to components of the assembly 65 such as an isolation valve (not shown) or to other surgical tools.

The coring assembly 65 also includes a conduit protection sheath 80 that nests slidably within the coring assembly housing 70. When attached to the remote cannulation assembly of the invention 10 such as is shown in FIG. 2, the sheath 80 is configured to be deployed from the coring assembly housing 70, through an isolation valve (not shown), and into a conduit (not shown) as described above. The sheath 80 serves to protect a conduit from damage caused by the cutting elements of the coring assembly 65 as they travel through such a conduit and other components of the coring assembly 65. As such, the sheath 80 is constructed from a material that resists such damage.

The coring assembly 65 also includes a blade 90. In this embodiment, the blade 90 is a cylindrical cutting tool having a sharp cutting edge 95. The blade 90 is nested slidably within the conduit protection sheath 80. The blade 90 is configured to be operated remotely, although it may also be used in surgeries in which conventional access to the heart is used. A core retainer 100 is nested within the cutter blade 90. The core retainer 100 has a helical coring blade 102 and a handle 104. The coring assembly 65 may also include a coring assembly cap 105 to seal the assembly 65 when it is first attached to the remote cannulation assembly 10.

In other embodiments of the invention, the cutter blade 90 may take different forms, including flexible cylindrical cutting tools, blades of various configurations such as rotatable blades, and alternative cutting tools such as hydrojet cutters. Additionally, the core retainer 100 may take different forms. The core retainer 100 may be a raised helical ridge attached to an inside face of the cutter blade 90. In such embodiments, the methods of coring are slightly altered because the core retainer 100 is advanced along with the cutter blade 90.

In some embodiments of the coring assembly 65, a port 102 may be provided at or near the tip of the core retainer 100. This port 102 may be connected to a pressure monitoring or fluid sampling port near an outside end of the coring assembly 65. Monitoring of the pressure and sampling of the fluid present at the tip allow the operator of the coring assembly 65 to know when the core retainer 100 has penetrated the wall of the heart 2. Such monitoring helps to avoid damaging the interior of the heart 2 with the core retainer 100. Similarly, having established the needed depth, the blade 90 may be monitored to assure that it is not advanced too far into the heart 2, similarly preventing damage. An endoscope could be used with port 102. An endoscope could be used to insert a physiologically acceptable fluid into the body part to assure that a positive pressure is present.

Figure 7:
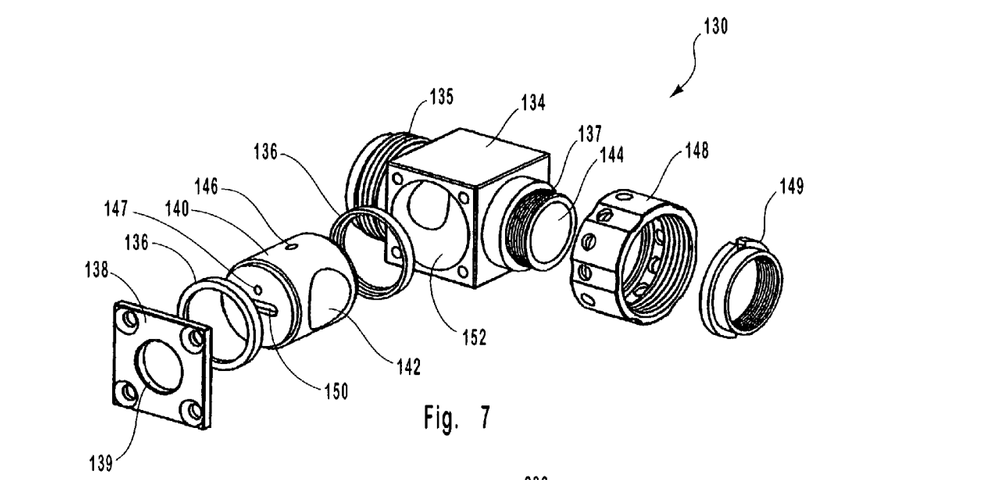
FIG. 7 is an exploded perspective view of an alternative isolation valve according to the invention.

Referring now to FIG. 7, an alternative embodiment of an isolation valve 130 is shown in perspective. The isolation valve 130 functions using a rotatable valve gate 140 that is rotatable within a housing 134. When the gate passage 142 of the valve gate 140 is aligned, at least in part, with the flow path 144 of the housing 134, then the valve 130 is in an open configuration. The gate 140 may be rotated by turning a tool inserted into notch 150 of the gate 140. When turned 90° in any direction from a fully open position, the valve 130 will be in a closed position. In this position, de-airing ports such as ports 146 may be exposed to the flow path 144. This allows for de-airing of the flow path 144 and the ends of the system, including the inflow and outflow conduits and the assist pump. The rotatable valve gate 140 may also include a de-airing aperture 147 to aid in de-airing the valve.

The rotatable valve gate 140 of the isolation valve 130 is contained in a housing 134. The valve gate 140 is mounted in a bore 152 in the housing 134, and sealed at the ends with seals 136. The resulting assembly is retained in place using a housing plate 138, which attaches to the housing 134 in a secure manner. The housing plate 138 includes an access port 139 that allows access to the notch 150 of the rotatable valve gate 140, thus allowing the position of the valve gate 140 to be changed.

The valve 130 may be mounted to other portions of the system including inflow and outflow conduits, as well as a heart- or ventricular-assist-pump. Attachment to these components may be accomplished in a variety of ways taught herein, as well as ways known in the art. Both sides of the valve 130 may include identical attachment features, or each side may be equipped with differing features to allow the attachment of specialized portions of the apparatus or equipment to the valve 130. FIG. 7 shows a valve 130 having different attachment features on two ends. On a first face of the valve 130, a screw ring 148 and an adapter tube 149 may be attached to the housing 134 via threads 137. In the embodiment shown, a second face of the valve 130 has a larger set of threads 135 adapted to be attached to a component of a different size.

This embodiment of the isolation valve 130 of the invention is intended to be placed and left within the body following heart coring, heart cannulation, and installation of an assist device. In such post-surgical use, the valve 130 is placed in its open configuration with the gate passage 142 at least substantially aligned with the flow path 144, thus allowing clear flow of blood through the valve 130.

Figure 8:
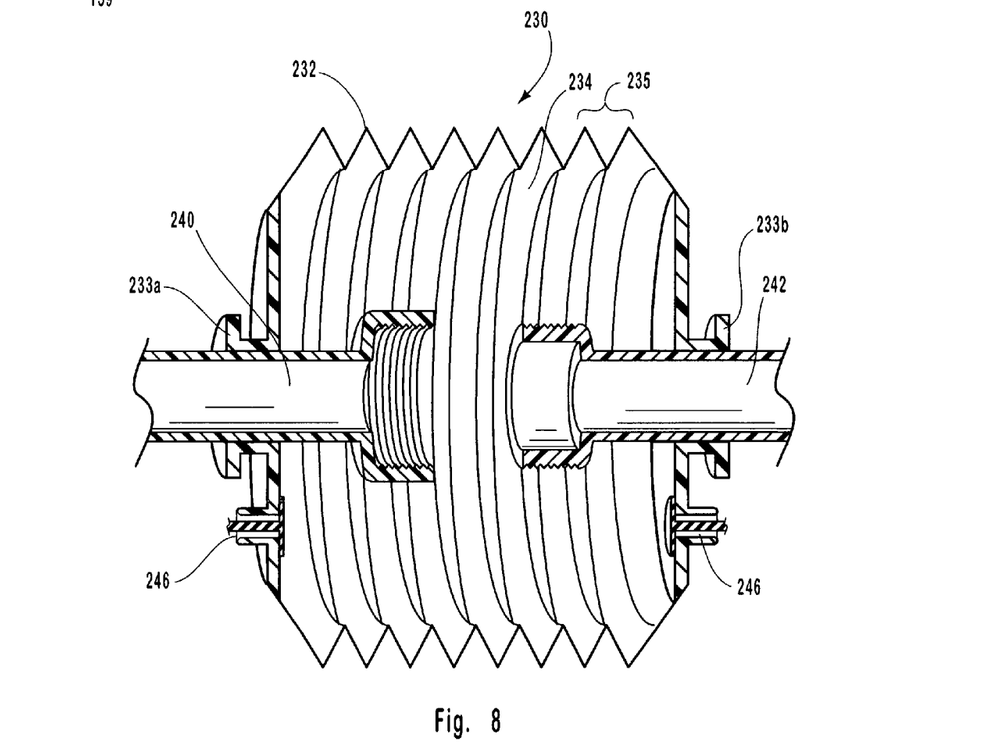
FIG. 8 is a cross-sectional view of another alternative isolation valve of the invention.

Referring now to FIG. 8, another embodiment of the isolation valve 230 of the invention is shown in a cross-sectional view. In this figure, the valve 230 includes a flexible sealable cuff 232 having end seals 233a, 233b that can be placed about portions of the system while they are being joined to each other. The cuff 232 may have features such as accordion pleats 235 to increase its flexibility and give expandability to the cuff 232. The cuff 232 defines an interior space 234. In FIG. 8, the cuff 232 is shown sealably attached about an end of the conduit 240 and ends of the pump.

The cuff 232 may be sealed in such a fashion that gases and liquids cannot penetrate the cuff 232. At the ends, the end seals 233a, 233b connect in this manner. The cuff 232 is sealed by applying a clamping force to the region between the end seals using clamps, forceps, or other similar tools. The cuff 232 is flexible in its construction such that clamping it shut prevents passage of fluid through the cuff 232. This feature may be useful prior to the establishment of a seal about an end of the cuff 232 prior to the establishment of an air-free environment inside of the cuff 232.

The cuff 232 may be a single unitary component that is cut away from the completed assembly after use. Alternatively, the cuff 232 may be composed of multiple segments capable of being sealably united to increase convenience of use and allow use of the assembly to remove or repair connections or conduits of the LVAD assembly.

The cuff additionally includes at least one de-airing port 246 to allow the interior 234 of the cuff 232 to be de-aired. Preferably, the cuff contains at least two de-airing ports 246. These de-airing ports 246 allow saline or another suitable fluid to be pumped into the cuff 232 and for all air to be removed from the cuff 232 to allow sealed joining of the components such as the conduit 240 and the pump 242.

In use, the cuff 232 is sealably attached about the components to be joined such as the end of a conduit 240 and the VAD 242. This is generally done while these components are occluded. This occlusion may be accomplished by simply clamping the conduit 240 closed. The cuff 232 is then sealed, and the interior space 234 defined within the cuff 232 is de-aired using saline or another physiologically-suitable fluid. At this point, the components may be opened such that they are in fluid connection with the interior of the cuff 234 and each other. The components may then be connected to each other within the flexible cuff 232 without the introduction of emboli into the system.

The cuff 232 may be assembled about previously installed components of the system to allow completion of initial installation, or to allow removal and/or replacement of the components. Specifically, the cuff 232 may be attached about an established joint and de-aired. The joint may then be disrupted, and the previously-joined components separated. The cuff 232 may then be subdivided using tools such as forceps to separate the disrupted components. One end of the cuff may be retained in a sealed configuration while the other end of the cuff 232 may be opened and the part inside replaced. Following this, the open portion of the cuff 232 could be re-sealed, de-aired, and then restored to fluid communication with the rest of the cuff 232 by release of the forceps. The new component may then be attached in a sealed environment.

Referring now to FIGS. 1-8, the invention further provides a method for remotely cannulating a heart 2 to affect an aortic anastomosis 50 as seen in FIG. 1. The method may be performed using the various tools and devices discussed in detail above. Specifically, the method may be accomplished remotely: from a distance of up to several inches away from the heart 2. This may eliminate the need for performing a sternotomy or thoracotomy on the patient. The method of the invention is discussed herein in the context of the implantation of a left ventricular assist device, or "LVAD." Such a device is implanted and connected to a heart's left ventricle 4 and to the aorta 51. It should be understood that other connection locations may be used for pumps such as right ventricular assist devices, or "RVADs" and other such assist or replacement devices. Despite this, the steps of the invention would be similar when applied to RVADs and other heart-assist or replacement devices, and are thus included herein. The precise sequence of steps of the method may be changed without substantially changing the procedure and its advantages.

A first step of the method is to connect an apical ring 12 to the heart 2 as illustrated in FIG. 1 to provide an anchor for the cannula 26. The apical ring 12 attaches to the heart 2, and a locking ring 18 may be placed either within or over the apical ring 12 to interact with the cannula 26. Specifically, when a cannula 26 passes through the locking ring 18, it expands the ring 18, locking the teeth 29 of the ring into the locking stem 16 of the apical ring 12. As this occurs, the locking ring 18 may snap into place in a groove 25 on the cannula 26 as seen in FIG. 2 to lock the cannula 26 into place. The connection of the apical ring 12 to the cannula 26 is a sealed connection such that blood or other fluids cannot escape at the joints. Further, the apical ring 12 may be sealed to the heart 2 such that blood, air, and other fluids cannot penetrate. This may be accomplished through the use of topical surgical sealants such as collagen glue or the like.

The apical ring 12 often includes an attachment ring 14 of physiologically-acceptable felt by which the ring 12 may be attached to the body part. One currently preferred method for this attachment is to suture the apical ring to the apex of the heart 2 using long-handled, remote suturing devices such as would be used in minimally invasive surgery. Surgical staples or other means could also be used.

The apical ring 12 also includes a locking stem 16. The locking stem 16 may include slots 17 for engaging the locking ring 18. The locking ring 18 may have teeth 19 to fit in the slots 17 of the apical ring 12. These teeth 19 expand to fit into the slots 17 of the locking stem 16 to hold the cannula 26 in place.

Other means of attaching a cannula such as 26 to the apical cuff 12 could include surface features on the cannula 26 such as screw threads or other features that could be constructed to integrate with features on the apical ring 12. Specifically, the apical ring 12 may be provided with threads on an inside diameter to which the cannula 26 could be attached. It may also have external threads (or other attachment means) to which tools used in the cannulation process described herein may be attached.

The remote cannulation assembly 10 and the remote coring assembly 65 are next assembled. First, the remote cannulation 10 apparatus is assembled by connecting an apical cannula 26, an inflow conduit 20, an isolation valve 30, a remote coring assembly 65, and a remote cannulator housing 11 together. To begin the coring and cannulation process, the apical cannula 26 is advanced until its tip presses against the heart 2 in order to form a reasonably good liquid seal against the tissue of the heart muscle 2. This seal prevents excessive leakage of blood or saline solution as well as the introduction of air into the heart 2 when the apparatus 10 is filled with saline in a later step, and when the heart 2 is cored prior to cannulation.

After this simple pressure-based seal is formed, a pressurized source of sterile saline solution (or other physiologically appropriate fluid) is connected to an inlet valve on the remote cannulator housing. All air is purged from the housing, coring assembly 65 (such as coring assembly 65 of FIG. 6), isolation valve (such as valve 30 of FIG. 2), inflow conduit (such as conduit 20 of FIG. 1), and apical cannula (such as 26 of FIG. 1) by flushing the system with the fluid and allowing the air to be withdrawn. Next, a positive pressure is maintained with the saline solution such that if any leakage occurs from the housing or from the pressure seal with the heart 2, lost fluid will be replaced with saline. As the heart 2 is cored, and thereafter, it should be maintained with positive pressure by blood, saline, or any other physiologically appropriate fluid. This pressure is utilized to assist in continuous exclusion of air from the assembly 10.

As shown in FIG. 2, the inflow conduit 20 may be provided with an isolation valve 30 at the end opposite the heart 2 for use in closing the flow path when the coring assembly 65 (such as coring assembly 65 of FIG. 6) are removed. In some situations, a clamp could be used in lieu of an isolation valve 30. The tool insertions outlined in the next several steps are done through the inside of an open isolation valve 30 (or equivalent clamp).

To begin coring, the conduit protection sleeve 80 of FIG. 6 is advanced inside the full length of the inflow conduit 20 and cannula 26 to protect them from being cut by the blade 90. The blade 90 is next advanced inside the conduit protection sleeve 80. The core retainer 100 is moved forward inside the blade 90. The heart 2 (or other body part) is next cored from the inflow conduit 20 and any excised heart tissue is removed according to the following steps.

The core retainer 100 is first driven through the wall of the heart 2 until it enters the interior of the ventricle 4. To facilitate this, a port 102 may be provided at or near the tip of the core retainer 100. This port 102 may be connected to a pressure monitoring port near an outside end of the coring assembly 65 to monitor the pressure at the tip of the core retainer 100. Such a port 102 could also allow the use of an endoscope to establish the point at which the core retainer 100 breaks through the heart wall into the ventricle 4. This may allow the surgeon to know when to stop advancing the core retainer 100, thus avoiding damage to the interior of the heart 2.

The blade 90 is driven part way through the wall of the ventricle 4, thus partially coring the heart 2. Following this, the apical cannula 26 may be advanced as far as the partially cored heart wall will allow. The two preceding steps may be repeated until the blade 90 cuts completely through the wall of the ventricle 4 and the apical cannula 26 can be advanced inside the ventricle 4 to the desired final position. Alternatively, the blade 90 may simply be advanced completely through the wall of the ventricle 4, and after this the cannula 26 may be introduced. Following this, the cored tissue may be retracted from the heart 2 using the core retainer 100 and blade 90 in concert. Alternatively, the blade 90 may be left in place until the core is successfully removed.

In a final set of steps of the method of the invention, the blade 90 and core retainer 100 are removed, as is the conduit protection sheath 80. The system 10 may then be de-aired, and the isolation valve 30 of the system may be closed to seal the system 10 and the interior of the heart. First, the blade 90 and core retainer 100 are retracted past the isolation valve 30 into the cannulation tool housing 11 which is sealably attached to the isolation valve 30. The conduit protection sleeve 80 is next withdrawn past the isolation valve 30 into the cannulation tool housing 11. The isolation valve 30 is closed, or the inflow conduit 20 is clamped off. Lack of air in the cannulation assembly 10 may be assured by applying suction to the heart side de-airing port(s) 46 as shown in FIG. 2 of the isolation valve 30 until all air is removed. Following this, the de-airing ports 46 are sealed off. The remote cannulator housing 11 and all the parts inside it (including the apical wall core) may then be removed.

To complete the installation of the assist device 52, the aortic anastomosis 50 is completed by connecting the outflow conduit 54 as seen in FIG. 1 to the aorta 51. This step is performed using any of the common anastomotic techniques known in the art. Minimally invasive methods are desirable in the methods of the invention. Following this, the outflow conduit 54 may be de-aired by allowing reverse blood flow through the outflow conduit 54 as the aortic wall 51 is unclamped. Air is removed by means such as providing an isolation valve similar to 30 and applying suction through a de-airing port 46 of the isolation valve 30.

The ventricular assist- or heart replacement-device 52, is then attached to the inflow conduit 20 of the cannulation assembly 10 and the outflow conduit 54 of the aortic anastomosis 50. First, the pump inlet 53 of the pump 52 is attached to the closed inlet isolation valve such as 30 of FIG. 2. Next, the pump outlet 55 is connected to a closed outlet conduit isolation valve such as 30 of FIG. 2 which is attached to the aorta 51 by means of the outflow conduit 54. The pump 52 is now connected to the patient's circulatory system. Flow through the pump 52 is prevented by the isolation valves such as 30 of FIG. 2, thus preventing the introduction of air from the pump 52 or the surroundings into the patient's circulatory system.

Following this, the pump 52 is de-aired by introducing saline solution into the de-airing port 46 of the inlet isolation valve such as 30 of FIGS. 2, 4, and 5, while withdrawing air (and saline) at the pump outlet isolation valve such as 30 of FIGS. 2, 4, and 5. If desired, the pump 52 may be operating during this step to aid the passage of air through to the outflow conduit 54. After air has been removed, the de-airing ports 46 may be closed in both isolation valves. The function of the pump 52 may then be observed by activating it and ensuring proper operation.

To begin use, the isolation valves such as 30 of FIGS. 2, 4, and 5, on both ends of the pump 52 are opened to allow blood flow. In embodiments of this method, isolation valves such as 30 of FIGS. 2, 4, and 5; isolation valve 130 of FIG. 7, and isolation valve 230 of FIG. 8 may be used in the invention. Sealing connections are then made at inflow 53 and outflow 55 connections of the pump. At this point, the isolation valves may be disconnected and removed from the patient and all connections may be verified for completeness.

To remove the valves, the inflow conduit 20 and outflow conduit 54 are first connected to the pump 52 through the inside of the respective isolation valves. The isolation valve housings such as 34, 36 of FIG. 2 may then be removed from the pump inlet 53 and outlet 55, while the seal is retained. A screw ring such as 28 of FIG. 1 may then be attached to retain and fixate the pump 52 and conduits 20, 54. The pump 52 is now operating inside the patient's circulatory system and may be placed and restrained as the surgeon sees fit. The pump 52 is then operated as desired.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed and desired to be secured by U.S. Letters Patent is:

1. A cannulation assembly for cannulating a body part, the cannulation assembly comprising:
   a cannula; and
   an isolation valve in sealed fluid communication with the cannula, the isolation valve having an open position that permits fluid passage through the cannula and a closed position that substantially prevents fluid passage through the cannula, wherein the isolation valve comprises a flexible tubular housing having a first end and a second end, the first and second ends being configured to be sealably attached about at least one fluid conducting element, wherein the flexible housing may be sealed between the first and second ends by applying a clamping force between the first and second ends to substantially prevent fluid passage between the first and second ends of the conduit.

2. The cannulation assembly of claim 1, wherein the cannula is configured to be coupled to an attachment assembly on the body part to securely anchor it to the body part.

3. The cannulation assembly of claim 2, wherein the cannula is substantially cylindrical.

4. The cannulation assembly of claim 2, wherein the cannula includes threads.

5. The cannulation assembly of claim 2, wherein the cannula comprises a locking notch to allow it to be securely anchored to the attachment assembly on the body part.

6. The cannulation assembly of claim 1, wherein the cannulation assembly further comprises a conduit positioned after the isolation valve, the conduit being sealably attached to the isolation valve.

7. The cannulation assembly of claim 1, wherein the cannulation assembly further comprises a conduit positioned between the cannula and the isolation valve, the conduit being sealably connected to the cannula on a first end and to the isolation valve on a second end.

8. The cannulation assembly of claim 7, wherein the conduit is a flexible conduit.

9. The cannulation assembly of claim 7, wherein the conduit has a fixed shape.

10. The cannulation assembly of claim 1, wherein the tubular housing comprises at least one de-airing port for removing air from the tubular housing.

11. The cannulation assembly of claim 1, wherein the tubular housing is configured to be completely removed from a patient after use.

12. The cannulation assembly of claim 1, wherein the tubular housing is comprised of at least two segments that sealably link together.

13. The cannulation assembly of claim 1, wherein the tubular housing comprises two de-airing ports for removing air from the tubular housing.

14. A cannulation assembly for cannulating a body part, the cannulation assembly comprising:

an attachment assembly configured to be attached to the body part;

a cannula configured to be attached to the attachment assembly; and an isolation valve having an open configuration that permits fluid flow and a closed configuration that blocks fluid flow, the isolation valve including a flexible tubular housing having a first end and a second end, the first and second ends being configured to be sealably attached about at least one fluid conducting element, wherein the flexible housing may be sealed between the first and second ends by applying a clamping force between the first and second ends to substantially prevent fluid passage between the first and second ends of the conduit, and the tubular housing including at least one de-airing port for removing air from the tubular housing.

15. The cannulation assembly of claim 14, wherein the attachment assembly comprises an attachment ring capable of being attached directly to the body part and a locking stem for engaging the cannula.

16. The cannulation assembly of claim 15, wherein the cannula comprises external features configured to lock with the attachment assembly.

17. The cannulation assembly of claim 16, wherein the external features include a screw thread.

18. The cannulation assembly of claim 16, wherein the external features include a separate locking ring and a locking notch in the cannula for engaging the locking ring.

19. The cannulation assembly of claim 14, wherein the tubular housing is configured to be completely removed from a patient after use.

20. The cannulation assembly of claim 14, wherein the tubular housing iscomprised of at least two segments that sealably link together.

21. The cannulation assembly of claim 14, wherein the tubular housing comprises two de-airing ports for removing air from the tubular housing.

* * * * *